United States Patent

Cohen et al.

[11] Patent Number: 5,840,756
[45] Date of Patent: Nov. 24, 1998

[54] PHARMACEUTICAL COMPOSITION OF L-DOPA ESTER

[75] Inventors: Sasson Cohen, Tel Aviv; Sela Yoram, Raanana; Ruth Levy, Tel Aviv; Nava Shterman, Petach Tikva; Eldad Melamed, Mevasserett Zion; Dafna Atlas, Neve Granot, all of Israel

[73] Assignees: Teva Pharmaceutical Industries Ltd.; Yissum Research Development Company of the Hebrew University of Jerusalem, both of Jerusalem, Israel

[21] Appl. No.: 678,716

[22] Filed: Jul. 11, 1996

Related U.S. Application Data

[60] Provisional application No. 60/001,368 Jul. 21, 1995.
[51] Int. Cl.⁶ .................. A61K 31/24; A61K 31/195; A61K 31/16; A61K 31/135
[52] U.S. Cl. .................. 514/538; 514/565; 514/614; 514/654; 514/657
[58] Field of Search .................. 514/538, 565, 514/614, 654, 657

[56] References Cited

U.S. PATENT DOCUMENTS

| 4,259,314 | 3/1981 | Lowey | 424/19 |
|---|---|---|---|
| 4,424,235 | 1/1984 | Sheth et al. | |
| 4,680,323 | 7/1987 | Lowey | 524/43 |
| 5,354,885 | 10/1994 | Milman et al. | 560/43 |
| 5,607,969 | 3/1997 | Milman et al. | 514/538 |

FOREIGN PATENT DOCUMENTS

| 0610595 | 8/1994 | European Pat. Off. |
|---|---|---|

*Primary Examiner*—William R. A. Jarvis
*Attorney, Agent, or Firm*—John P. White; Cooper & Dunham LLP

[57] ABSTRACT

The present invention provides a pharmaceutical composition contains a therapeutically effective amount of L-DOPA ethyl ester and a carrier which comprises from 5.5 to 98.5% hydroxypropylmethyl cellulose, from 0.25 to 4.5% hydroxypropyl cellulose, and from 1 to 90% of a carboxyvinyl polymer.

16 Claims, 1 Drawing Sheet

PHARMACEUTICAL COMPOSITION OF L-DOPA ESTER

This application claims the benefit of priority of U.S. Provisional Application No. 60/001,368, filed Jul. 21, 1995, the contents of which are hereby incorporated by reference into the present application.

Throughout this application, various references are referred to within parenthesis. Disclosures of these publications in their entireties are hereby incorporated by reference into this application to more fully describe the state of the art to which this invention pertains.

BACKGROUND OF THE INVENTION

The present invention relates to a novel formulation of L-DOPA ethyl ester that provides an initial burst of levodopa followed by maintenance of a sustained level of said compound thus increasing the bioavailability of levodopa to a patient.

Levodopa, in combination with carbidopa or benserazide, remains one of the most effective therapies for Parkinson's disease (PD). Within five years after initiation of such a therapy, disabling motor fluctuations appear in about 50 percent of the treated patients (Wooten GF (1988). Ann Neurol. 24: 363–365). This disability appears as random periods of sudden and unexpected loss of efficacy of levodopa therapy aggravated with time, and has been termed the 'on-off' phenomenon. Several studies suggest that the motor fluctuations are directly related to the levels of plasma levodopa (Wooten GF supra). Various observations lend support to this contention, for example, gastric emptying in the elderly, particularly in PD (plasma deficiency) patients, is erratic, often much too slow to compensate for the plasma deficiency in levodopa at the 'end of dose' (Bozeman T, et al., (1990), Am J Gastroenterol 85: 1264 and Kurlan R, et al (1988) Neurology 38: 419–421). This effect, when coupled to the low water solubility of levodopa itself and to the usual retention in the stomach of particulate matter is expected to further decrease the rate of transfer of the ingested dose of levodopa from the gastrointestinal (GI) tract to the plasma (Kelly KA (1981). "Motility of the stomach and gastroduodenal junction", in Johnson LR, editor, Physiology of the Gastrointestinal Tract, Raven Press, New York, pp. 393–410). For almost any drug, the combined pharmacokinetics of a low absorption rate and a high elimination rate (as is the case of levodopa with a plasma half-life of about 1 hour) are conducive to plasma drug levels that are below the effective therapeutic range, hence treatment becomes ineffective.

Various procedures have been sought to remedy this situation. In some cases, direct instillation of a slurry of levodopa through a duodenal tube has given rapid relief from the 'off' state (Kurlan R, et al., (1986) Ann. Neurol. 20: 262–265 and Cedarbaum et al., (1990 Neurology 40: 887–995. In another approach, oral dosing with a dilute aqueous solution of levodopa appeared to be effective (Kurth MC, et al., (1993). Neurology 43: 1036–1039). Neither of these measures are practical enough to allow self-medication when urgently needed. When rapid relief is needed, the more common procedure is to recommend to the patient to crush the levodopa tablet before intake, so as to minimize the time required for its disintegration in the GI tract. The efficacy of this procedure has never been demonstrated.

A different approach for the maintenance of steady therapeutic levels of levodopa in the plasma of Parkinson's disease patients is the use of the levodopa/carbidopa combination in a controlled-release formulation. Such dosage form is currently available under the brand name SINEMET CR (Merck Sharpe & Dohme). SINEMET CR is supplied as sustained release tablets in two dosage forms—200/50 and 100/25 levodopa/carbidopa ratio. From the documented profile of SINEMET CR (Physicians Desk Reference (PDR), 48th Edition 1994, Medical Economics Data, N.J., USA), one can identify the major issues where this formulation has fallen short of the real needs in oral levodopa therapy i.e. rapid onset of action and sustained therapeutic effect. SINEMET CR provides the sustained effect but only at the expense of the latency of onset of drug action which is unduly long and also at the expense of bioavailability of the active constituent. This conclusion is borne out by the data reported (PDR 1994 supra) which may be summarized as follows:

The time to peak dose is given as 2 hours, as compared to 0.5 hour for SINEMET STD (standard formulation). Thus, premedication with SINEMET STD may be necessary before intake of the first daily dose, a measure not practical in rapid fluctuators and not consistent with patient compliance.

The duration of drug release is given as 4–6 hours which is acceptable, provided a dosage schedule of 3–4 tablets a day is given, but unacceptable in rapid fluctuators who require more dosing intervals per day. Also the usual transit time in the small intestine which is the site of absorption is 4 hours, so that some of the drug will be lost in the faeces.

In the elderly only 70–75% of the drug is bioavailable as compared to SINEMET STD, implying that the drug is not fully absorbed following poor release of levodopa over the 4 hour effective absorption interval. In the young this FIGURE drops to 44% indicating a relatively shorter residence time in the gastrointestinal (GI) tract. Bioavailability is also influenced by food intake so that plasma levels may fluctuate erratically, depending on meals.

Obviously, the combination of levodopa with a sustained-release base as in SINEMET CR has failed to provide the pharmacokinetic profile that is required for the control of plasma level fluctuations of levodopa, especially in rapid fluctuators.

There is therefore a need for a pharmaceutical composition that will increase the bioavailability of levodopa to a patient requiring such treatment, the existing compositions not providing sufficient sustained levels of levodopa to maintain a satisfactory level of treatment.

In an effort to provide pharmaceutical compositions that permit uniform and continuous dissolution of active materials, U.S. Pat. No. 4,259,314 (Lowey, 1981) discloses a composition comprising an active agent in admixture with from 80–95% hydroxypropylmethyl cellulose (HPMC) and 5–20% hydroxypropyl cellulose (HPC) having a moisture content of less than 1%. The formulation described therein is stated to be of especial use with hygroscopic therapeutic agents.

U.S. Pat. No. 4,680,323 (Lowey, 1987) describes a similar composition comprising a therapeutic agent in admixture with from 5.5–98.5% HPMC, from 0.25 to 4.5% HPC and from 1 to 90% of a carboxyvinyl polymer. Such a composition is described as providing "zero order" release rate of the therapeutic agent, i.e. a constant continuous release over a sustained period (12–24 hours).

U.S. Pat. No. 5,354,885 (Milman, 1994) discloses a composition containing a non-hygroscopic form of L-DOPA ethyl ester substantially free of L-DOPA suitable for pharmaceutical use. The L-DOPA ethyl ester described therein has been shown to function as a prodrug of levodopa whether delivered by the oral or parenteral route.

There is a further need for a stable pharmaceutical composition of L-DOPA ethyl ester that will provide an initial burst of levodopa to enable the patient to rapidly reach an "on" phase and then maintain a level of drug in the body to sustain the duration of the "on" phase. D. R. Cooper, et al. report that after oral administration L-DOPA ethyl ester and L-DOPA had the same time courses of action. (J. Pharm. Pharmacol. (1987) 39: 627–635, esp. p.634, left column, para. 4)). Thus, the initial burst of levodopa observed in the plasma of patients given a pharmaceutical composition of L-DOPA ethyl ester according to this invention, as compared to patients given L-DOPA in a comparable slow release formulation, is surprising.

SUMMARY OF THE INVENTION

The present invention relates to a pharmaceutical composition comprising L-DOPA ethyl ester in admixture with a carrier comprising from 5.5 to 98.5% hydroxypropylmethyl cellulose (HPMC) and from 0.25 to 4.5% hydroxypropyl cellulose (HPC) and from 1 to 90% of a carboxyvinyl polymer together with L-DOPA ethyl ester.

DETAILED DESCRIPTION OF THE INVENTION

Figure 1:
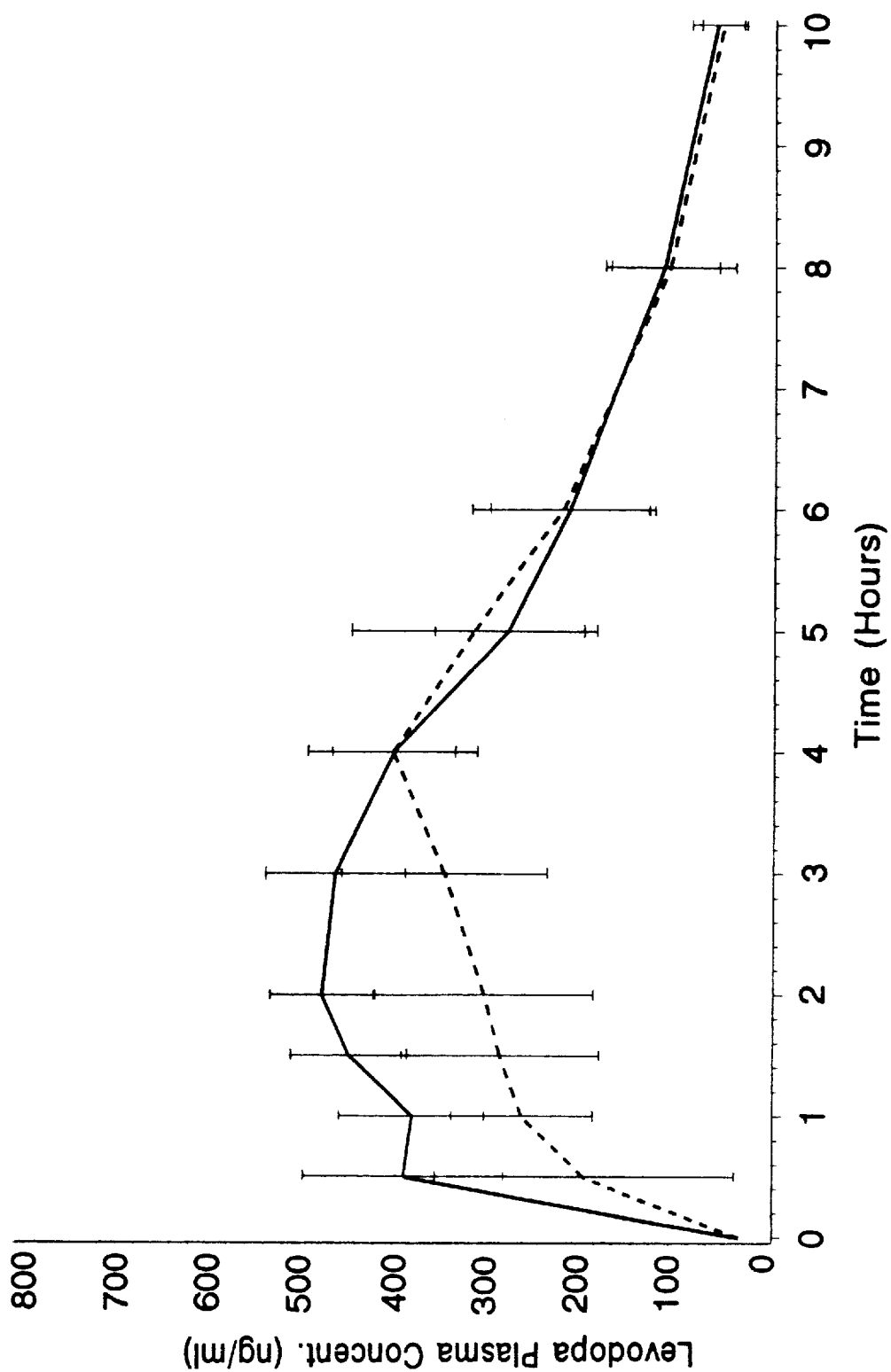
FIG. 1: Results of a randomized two-way crossover comparative study of slow release levodopa and slow release form of L-DOPA ethyl ester of the present invention, as described in Example 2. Shown are mean (±2 SE) levodopa plasma concentrations (ng/ml) of eight volunteers. The dashed line represents slow release levodopa; the solid line represents slow release L-DOPA ethyl ester.

The present invention provides a composition comprising L-DOPA ethyl ester in admixture with a carrier comprising from 5.5 to 98.5% hydroxypropylmethyl cellulose (HPMC) and from 0.25 to 4.5% hydroxypropyl cellulose (HPC) and from 1 to 90% of a carboxyvinyl polymer.

Preferably, the celluloses and carboxyvinyl polymer together form a dry carrier which in turn is mixed with the L-DOPA ethyl ester.

Preferably, the carrier comprises from 50 to 98.5% hydroxypropylmethyl cellulose (HPMC), from 1 to 3% hydroxypropyl cellulose (HPC) and from 1 to 50% of a carboxyvinyl polymer.

The carrier may be comprised of from 2–65% HPMC having a viscosity of about 50 centipoise for a 2% solution at 20° C., from 3–85% HPMC having a viscosity of about 4,000 centipoise for a 2% solution at 20° C., from 2–40% HPMC having a viscosity of about 15,000 centipoise for a 2% solution at 20° C. and from 0.5–40% HPMC having a viscosity of about 100,000 centipoise for a 2% solution at 20° C., together with from 0.25 to 4.5% hydroxypropyl cellulose (HPC) and from 1 to 90% of a carboxyvinyl polymer HPMC having a viscosity of about 30,000 to 40,000 centipoise for a 3% by weight neutralized solution. Preferably, the hydroxypropyl cellulose used has a viscosity of about 50 to 4,500 centipoise when measured as a 2% by weight aqueous solution.

HPMC having viscosities of about 50 and 4,000 centipoise for a 2% solution at 20° C. are known and commercially available as METHOCEL E-50 and E-4M respectively (Dow Chemical Company registered trademark). HPMC having viscosities of about 15,000 and 100,000 centipoise for a 2% solution at 20° C. are known and commercially available as METHOCEL K-15M and K-100M respectively (Dow Chemical Company RTM). Hydroxypropyl cellulose as used in accordance with the present invention is known and commercially available as KLUCEL (a Hercules Inc. registered trademark).

Suitable carboxyvinyl polymers of use in the present invention include polymers of acrylic acid or polyacrylic acid, cross linked with a polyalkenyl polyether. Such polymers are available from the BF Goodrich Company under the trademark CARBOPOL. They have viscosities of 29,000 to 40,000 centipoise for a 3% by weight aqueous solutions. Such polymers are weak acids and react to form salts.

The L-DOPA ethyl ester used in the compositions of the present invention is preferably that as described in U.S. Pat. No. 5,354,885, the contents of which are hereby incorporated by reference, and is prepared according to the method described therein. Preferably the L-DOPA ethyl ester is highly purified, stable non-hygroscopic and crystalline. The therapeutically effective amount of L-DOPA ethyl ester is preferably an amount of from 10 to 1,000 milligram equivalents of levodopa or more preferably, the therapeutically effective amount of L-DOPA ethyl ester is from 50 to 250 milligram equivalents of levodopa. In an embodiment of this invention the composition comprises from about 80 mg to about 300 mg L-DOPA ethyl ester.

An embodiment of the above-described composition comprises 228 milligrams L-DOPA ethyl ester and a carrier, wherein the carrier comprises 96 percent hydroxypropylmethyl cellulose, 3 percent hydroxypropyl cellulose and 1 percent carboxvinyl polymer by weight of the carrier.

In an embodiment of this invention, 62 percent of the hydroxypropylmethyl cellulose has a viscosity of about 50 centipoise for a 2 percent solution at 20° C.; and 34 percent of the hydroxypropylmethyl cellulose has a viscosity of about 4,000 centipoise for a 2 percent solution at 20° C.

The composition of the present invention may optionally contain further ingredients such as sweeteners, binders, flavoring agents or an antioxidant. If an antioxidant is added, it is preferable that it is selected from the group comprising butylated hydroxy toluene, butylated hydroxy anisole, ascorbic acid, vitamin E or sodium metabisulphite.

The composition of the present invention may optionally further contain an additional active agent such as an inhibitory amount of a decarboxylase inhibitor such as carbidopa or benserazide, or a monoamine oxidase type B inhibitor (MAO-B inhibitor), such as selegeline or (R)-N-propargyl-1-aminoindan. Other decarboxylase inhibitors and MAO-B inhibitors are also known to those of skill in the art and may be used in the pharmaceutical composition which is described herein. (For MAO-B inhibitors see, for example, Youdim, et al. Chapter 3 of Handbook of Experimental Pharmacology Vol. 90/I (1988), Trendelenburg and Weiner, eds.).

The mixtures of HPMC, HPC and the carboxyvinyl polymers are prepared by methods familiar to those skilled in the art, for example, as described in U.S. Pat. No. 4,680,323, the contents of which are hereby incorporated by reference. Thus, the components are added to one another in the desired proportions and thoroughly mixed to form a uniform composition. Thereafter from 80 to 300 mg of L-DOPA ethyl ester are added to the carrier and the pharmaceutical composition is compressed and shaped into a conventional pharmaceutical form.

The conditions under which the composition is compressed will influence the final form of the composition. Thus, if compressed under low pressure, a trouche or buccal tablet can be prepared capable of being sucked or used in the mouth. If higher pressures are used a harder composition can be prepared suitable for rectal or vaginal application. The final products may additionally contain other adjuvants such as stabilizers, preservatives, coloring agents or sweetening agents.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

In the following examples, the carrier composition was prepared by mixing the components in the desired proportion in a mixing bowl. The mixture was thoroughly stirred to achieve a uniform mixture and thereafter the desired amount of L-DOPA ethyl ester and other adjuvants or excipients were added in the amounts indicated.

The carrier, excipients and L-DOPA ethyl ester were then thoroughly mixed and compressed into tablets on a 40 kilo-Newton compressor at maximum compression.

EXAMPLE 1

Composition of L-DOPA ethyl ester tablets

|  | mg/tablet | % carrier |
|---|---|---|
| L-DOPA ethyl ester | 228.0 |  |
| KLUCEL LF | 6.84 |  |
| 3% |  |  |
| CARBOPOL 934 P | 2.28 |  |
| 1% |  |  |
| METHOCEL E-50 PREMIUM | 141.36 | 62% |
| METHOCEL E-4 PREMIUM | 77.52 | 34% |
| ethylcellulose NF | 6.0 |  |
| Sodium metabisulphite | 1.2 |  |
| microcystalline cellulose NF | 73.5 |  |
| colloidal dioxide NF | 2.8 |  |
| Magnesium stearate | 6.5 |  |

EXAMPLE 2

Comparison of slow release levodopa and the slow release form of L-DOPA ethyl ester of the present invention.

A randomized two-way crossover comparative study was performed to compare the release profiles of a formulation containing levodopa and the slow release composition of L-DOPA ethyl ester of the present invention. The levodopa was made up into 200 mg (equivalent) tablets in the same manner as the L-DOPA ethyl ester tablets were described in Example 1.

Eight fasting healthy adults each received a single oral dose of a formulation as in Example 1 containing 228.4 mg levodopa ethyl ester (equivalent to 200 mg levodopa), or a formulation as in Example 1 containing 200 mg levodopa in place of the levodopa ethyl ester. All subjects received two days pretreatment of an oral formulation of carbidopa. Each patient received one of the formulations and then the alternative formulation after a one week washout period.

Blood samples were taken from patients initially prior to dosing to obtain a baseline reading and then at 0.5, 1, 1.5, 2, 3, 4, 5, 6, 8, and 10 hours post dosing. The subjects fasted overnight (10 hours) prior to dosing and were allowed to commence eating normal meals 4 hours after dosing.

Blood levels of levodopa in the subjects were measured and the results are shown in FIG. 1. From FIG. 1 it can easily be seen that in comparison to the levodopa slow release formulation, the composition of the present invention provides an early "burst" of levodopa followed by the maintenance of a sustained level of drug over the following hours. Such a composition will clearly benefit patients suffering from Parkinson's Disease and, as discussed above fulfills the long felt want for such a composition by increasing the bioavailability of levodopa.

EXAMPLE 3

The following carriers (A-D) were prepared as described in Example 1 to a weight of 228.0 mg and each combined with 228.0 mg L-DOPA ethyl ester, 9.0 mg ethylcellulose, 2.0 mg sodium metabisulphite, 4.8 mg Syloid and 9.6 mg sodium stearoyl fumarate to form 481.4 mg tablets. Each formulation was then tested in a dissolution bath (USP, Apparatus 2 (Paddle) 75 rpm). The release profile for each formulation over a 12 hour period is shown in Table 2 below.

TABLE 1

Percent composition of carrier

|  | A | B | C | D |
|---|---|---|---|---|
| Methocel E-50 | 0.7 | 11.75 | 1.6 | 1.3 |
| Methocel E-4M | 3.5 | 0.75 | 75.2 | 1.9 |
| Methocel K15M | 2.45 | 3.0 | 1.6 | 1.9 |
| Methocel K100M | 0.35 | 9.5 | 1.6 | 88.3 |
| Total HPMC | 7.0 | 25.0 | 80.0 | 94.0 |
| Klucel | 3.0 | 0.25 | 1.0 | 5.0 |
| Carbopol | 90.0 | 74.75 | 19.0 | 1.0 |

TABLE 2

Dissolution of Tablets A–D(n = 6)

| Time (Hr) | A | B | C | D |
|---|---|---|---|---|
| 2 | 31.0 | 29.9 | 33.7 | 34.6 |
| 5 | 50.9 | 52.8 | 59.3 | 60.8 |
| 9 | 72.2 | 72.3 | 82.7 | 84.6 |
| 12 | 91.2 | 87.2 | 94.8 | 96.1 |

What is claimed is:

1. A pharmaceutical composition comprising a therapeutically effective amount of L-DOPA ethyl ester and a carrier, wherein the therapeutically effective amount is an amount effective to provide an early burst of levodopa followed by the maintenance of a sustained level of levodopa and wherein the carrier comprises from 5.5 to 98.5 percent hydroxypropylmethyl cellulose; from 0.25 to 4.5 percent hydroxypropyl cellulose; and from 1 to 90 percent of a carboxyvinyl polymer by weight of the carrier.

2. The composition of claim 1, wherein the carrier comprises from 50 to 98.5 percent hydroxypropylmethyl cellulose; from 1 to 3 percent hydroxypropyl cellulose; and from 1 to 50 percent of a carboxyvinyl polymer.

3. The composition of claim 1, wherein the carrier comprises from 2 to 65 percent hydroxypropylmethyl cellulose having a viscosity of about 50 centipoise for a 2 percent solution at 20° C.; from 3 to 85 percent hydroxypropylmethyl cellulose having a viscosity of about 4,000 centipoise for a 2 percent solution at 20° C.; from 2 to 40 percent hydroxypropylmethyl cellulose having a viscosity of about 15,000 centipoise for a 2 percent solution at 20° C.; and from 0.5 to 40 percent hydroxypropylmethyl cellulose having a viscosity of about 100,000 centipoise for a 2 percent solution at 20° C.

4. The composition of claim 1, wherein the hydroxypropyl cellulose has a viscosity of about 50 to 4,500 centipoise for a 2 percent by weight aqueous solution.

5. The composition of claim 1, wherein the carboxyvinyl polymer has a viscosity of about 29,000 to 40,000 centipoise for a 3 percent by weight neutralized solution.

6. The composition of claim 5, wherein the carboxyvinyl polymer is a polymer of acrylic acid or a polymer of polyacrylic acid, cross-linked with a polyalkenyl polyether.

7. The composition of claim 1, wherein the L-DOPA ethyl ester is present in an amount from about 80 milligrams to about 300 milligrams.

8. The composition of claim 1, comprising 228 milligrams L-DOPA ethyl ester and a carrier, wherein the carrier comprises 96 percent hydroxypropylmethyl cellulose, 3 percent hydroxypropyl cellulose and 1 percent carboxvinyl polymer by weight of the carrier.

9. The composition of claim 8, wherein 62 percent of the hydroxypropylmethyl cellulose has a viscosity of about 50 centipoise for a 2 percent solution at 20° C.; and 34 percent of the hydroxypropylmethyl cellulose has a viscosity of about 4,000 centipoise for a 2 percent solution at 20° C.

10. The composition of claim 1, further comprising an antioxidant.

11. The composition of claim 10, wherein the antioxidant is selected from the group consisting of butylated hydroxy toluene, butylated hydroxy anisole, ascorbic acid, vitamin E, and sodium metabisulphite.

12. The composition of claim 1, further comprising an inhibitory amount of a decarboxylase inhibitor.

13. The composition of claim 12, wherein the decarboxylase inhibitor is carbidopa or benserazide.

14. The composition of claim 1, further comprising a monoamine oxidase type B inhibitor.

15. The composition of claim 12, wherein the monoamine oxidase type B inhibitor is selegeline or (R) -N-propargyl-1-aminoindan.

16. A method of treating Parkinson's Disease in a patient in need thereof comprising administering to the patient a therapeutically effective amount of the pharmaceutical composition of claim 1.

* * * * *